United States Patent [19]

Dalton

[11] Patent Number: 4,681,570
[45] Date of Patent: Jul. 21, 1987

[54] PERITONEAL CATHETER

[76] Inventor: Michael J. Dalton, 9432 Monticello Ave., Evanston, Ill. 60203

[21] Appl. No.: 813,418

[22] Filed: Dec. 26, 1985

[51] Int. Cl.⁴ .............................................. A61M 27/00
[52] U.S. Cl. ................................... 604/282; 604/281
[58] Field of Search .............. 604/282, 281, 280, 264, 604/268, 175, 29

[56] References Cited

U.S. PATENT DOCUMENTS 3,920,023 11/1975 Dye et al. ........................ 604/281 X
4,531,933 7/1985 Norton et al. .................. 604/281 X
4,579,555 4/1966 Russo ................................. 604/282

FOREIGN PATENT DOCUMENTS 1263097 7/1960 France ................................ 604/281

Primary Examiner—Stephen C. Pellegrino
Attorney, Agent, or Firm—R. L. Hansen

[57] ABSTRACT

A body-implantable catheter which can be employed for peritoneal dialysis and the like includes a flexible, elongated, perforated tube, together with means for urging at least a portion of the tube into a tightly wound cylindrical helix configuration.

10 Claims, 6 Drawing Figures

PERITONEAL CATHETER

This invention is in the field of body-inserted catheter structures; specifically, the invention relates to catheters having integral anticlogging means and, more specifically, to such catheters which are especially suitable for insertion into the peritoneal cavity for peritoneal dialysis and the like.

Hemodialysis has been employed for many years in the treatment of advanced renal disease, but the technique is not without difficulties. More recently, peritoneal dialysis has gained favor in the management of renal failure. In its simplest terms, the latter treatment requires flooding the peritoneal cavity with a sterile dialyzing fluid, allowing the fluid to absorb toxins from the blood stream by osmosis through the abdominal capillaries, and then draining the spent fluid from the cavity. The procedure is repeated until dialysis is complete. A catheter left in the cavity, to which percutaneous connection can be made periodically, allows dialysis to be carried out as often as necessary with minimal patient discomfort.

The desirability of maintaining a catheter in the peritoneal cavity is manifested in other situations as well. For example, the treatment of certain abdominal cancers is facilitated by employing a catheter to introduce a fluid containing a chemotherapeutic agent into the peritoneal cavity. After a time, the fluid is withdrawn through the catheter. This procedure may be repeated periodically for some time. An indwelling catheter left in the cavity simplifies the procedure.

The use of a peritoneal catheter carries its own set of problems. The peritoneum and peritoneal cavity can easily become the site for infection introduced by the catheter. Further, even if the catheter delivers the fluid efficiently into the peritoneal cavity, it may not be effective in draining the spent fluid from the body. This type of failure is most often encountered when the catheter is left in the body for a prolonged period of time. When the catheter fails to deliver fluid to or from the cavity after a period of time, it is often due to the fact the catheter has become clogged by membranous adhesions, scar tissue, or omentum. This problem has been recognized in the prior art for some time.

For example, after acknowledging the problem, U.S. Pat. No. 4,278,092 advises it be side-stepped by simply providing for replacement of the clogged catheter. U.S. Pat. No. 4,368,737 addresses this type of catheter obstruction by providing a disc-like structure at the distal end of the catheter which is placed in the abdomen against the peritoneum so as to avoid contact with the bowel and associated omentum. According to U.S. Pat. No. 4,391,276, the clogging problem can be solved by masking fluid delivery holes in the catheter with protrusions which tend to keep tissue away from the openings.

In U.S. Pat. No. 4,437,856 the clogging problem is attributed to close contact between the catheter and intestine; an expansible balloon-like catheter terminus is accordingly provided. U.S. Pat. No. 4,488,877 addresses the problem by designing the catheter to remain near the peritoneum wall, effected by giving the catheter a coiled configuration, and by making the catheter easy to replace if it becomes clogged.

None of the aforesaid approaches to the problem has been satisfactory, and the peritoneal catheter usually selected in clinical practice is the standard Tenckhoff catheter, in which no attempt is made by design to avoid clogging with tissue. The catheters which are intended to remain near the peritoneum, avoiding the intestines and pelvic gutter, are generally unsatisfactory because drainage from the peritoneal cavity is inefficient.

Accordingly, it is an object of the instant invention to provide a catheter which is suitable for implantation and long-term use in the peritoneal cavity and which tends to avoid the problem of clogging with tissue. It is another objective to provide a peritoneal catheter which is effective for the drainage of spent dialysate.

These objectives are attained in a catheter which includes a flexible, elongated tube with perforations in the wall of the tube to pass fluid to or from the tube's lumen and protrusions within the lumen to prevent collapse of the tube under a pressure gradient, together with means for urging at least a portion of the tube into a tightly wound cylindrical helix configuration.

In operation, the helix core provides a secondary fluid channel which acts as a sump for spent fluid, while pressure in the tube, impelling the helix to unwind, tends to free the tube perforations from organic deposits.

This invention, including the manner of making and using it, will be clarified by reference to the drawings which accompany this specification and to the detailed description which follows.

Figure 1:
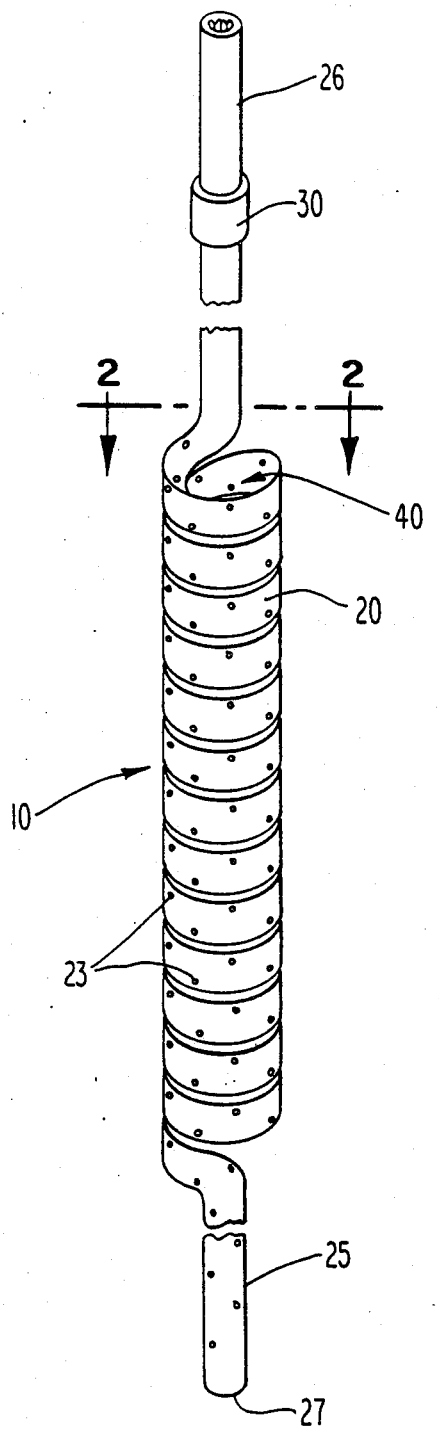
FIG. 1 is a perspective side view of one embodiment of the catheter of this invention, including certain optional features.
Figure 2:
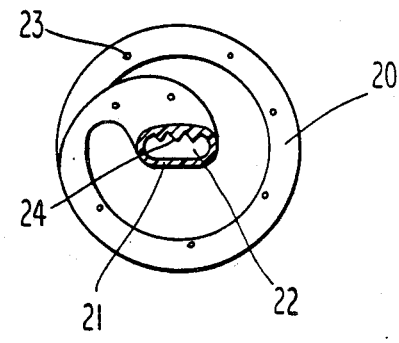
FIG. 2 is a cross-sectional view of the catheter of FIG. 1 taken along line 2—2 of FIG. 1.

With reference first to the embodiment illustrated in FIGS. 1-2, catheter 10 includes tube 20, a portion of which is urged into a tightly wound cylindrical helix configuration, providing secondary channel 40. Tube 20 may be open at distal terminus 27, but is preferably restricted or entirely closed to force the flow of fluid into or from lumen 22 primarily through perforations 23 in tube wall 21. Protrusions, which may be present in the form of longitudinal ribs 24, prevent collapse of the tube if a negative pressure gradient is established across wall 21; e.g., by applying suction to the tube to withdraw spent fluid.

Figure 3:
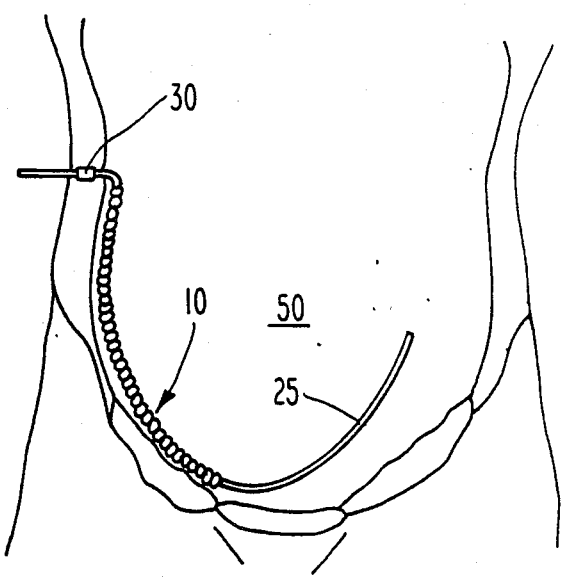
FIG. 3 is a partially cut away ventral view of the human abdomen showing placement therein of a catheter of this invention.

A substantially straight tail 25 is optionally provided between the helix portion and the distal terminus. This section is intended to reach an area of limited access away from the pelvic gutter of peritoneal cavity 50 as shown in FIG. 3. Such an area of limited access may arise, for example, from loculation which can occur in oncology patients. The proximal end 26 of the tube is preferably adapted to mate with a percutaneous fitting near the surface of the body or to connect to a subcutaneous reservoir of the type disclosed in U.S. Pats. No. 4,464,178 or 4,490,137. A number of suitable percutaneous fittings have been described; e.g., in the cited prior art which provides for catheter replacement. Cuff 30, made of polyester, for example, is optionally provided to foster tissue ingrowth and anchorage.

Tube 20 can be constructed of any of several commercially available, flexible, biocompatible materials, such as silicone or polyurethane thermoformable elastomer. Although the cross-section of the tube is not critical; e.g., it may be circular in cross-section, it is preferably of oval cross-section with relatively flat surfaces; e.g., 0.5 cm wide and 0.25 cm deep with a wall thickness of about 0.06 cm. In any case, it is necessary to provide means for urging at least a portion of the tube into a tightly wound, cylindrical helix configuration. For example, as in the embodiment of FIGS. 1 and 2, an elastomeric tube can be produced as a straight extrusion, then wound into the desired cylindrical helix configuration, and urged to remain in that configuration by vulcanizing the wound tube.

In a typical catheter of this invention the helical section is about 15-20 cm long, with a helix diameter of about 1.0 cm and about 0.06 cm between windings; tail 25 is about 10 cm in length, and proximal end 26 is about 10-15 cm long, all dimensions depending, of course, on the size of the patient. The windings of the helix are closely spaced to prevent invasion of secondary channel 40 by omentum. Although the catheter is long enough to extend through the pelvic gutter as shown in FIG. 3, it should be be as short as possible, consistent with that objective, in order to avoid knotting on itself and strangling an organ or part of the intestine.

The size, number and location of perforations 23 will vary with tubing size and elasticity. Operationally, the perforations must be sufficiently large to provide good flow, but small enough to prevent omentum and adhesions from invading the catheter. In general, there will be perforations both within the secondary fluid channel and on the outside of the helix. The perforations can range in diameter from about 0.01 to 2.0 mm, depending on their number. Perforations about 0.8 mm in diameter, staggered about the longitudinal center line of the tube on the inside and outside of the helix and spaced apart about 1.3 cm, are satisfactory. Preferably, the perforations are closer together approaching the distal end of the helix.

Figure 4:
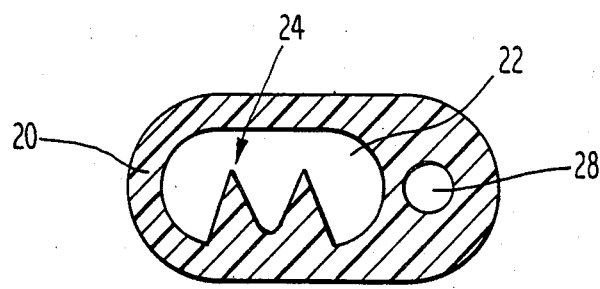
FIG. 4 is a cross-sectional view of the tube employed in another embodiment of this invention.
Figure 5:
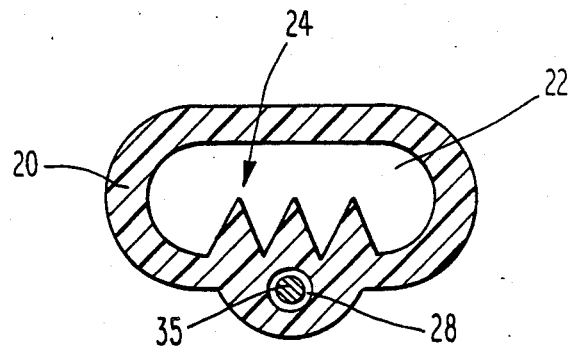
FIG. 5 is a cross-sectional view of the tube employed in yet another embodiment of this invention.
Figure 5A:
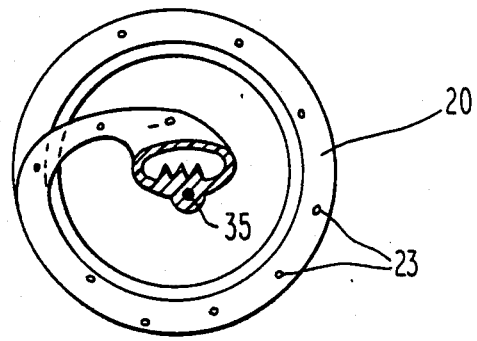
FIG. 5A is a cross-sectional view like FIG. 2, but showing the embodiment of FIG. 5.

FIGS. 4, 5 and 5A illustrate embodiments in which alternate means for urging tube 20 into a helix configuration are provided. In these embodiments biocompatible, helical spring wire 35 is threaded through longitudinal passage 28 which is provided in tube 20. The restoring spring force urges tube 20 into a tightly wound helical configuration. Other means for urging the tube into a helix configuration will be evident to those skilled in the art.

In the event it becomes necessary to remove the catheter of this invention from the patient, it can simply be withdrawn, since the helix readily unwinds. In embodiments which incorporate a helical spring wire, the wire can be withdrawn prior to removing the catheter from the patient.

It will be evident that other variations, not specifically illustrated, are within the contemplation of this invention and the scope of the following claims:

What is claimed is:

1. A body-implantable catheter especially suited for percutaneous communication with the peritoneal cavity which comprises a flexible, elongated tube with perforations in the wall thereof to pass fluid to or from the lumen of said tube, and protrusions within said lumen to prevent collapse of said tube under a negative pressure gradient; together with means acting on said tube for urging at least a central portion of said tube into a tightly wound cylindrical helix configuration with closely spaced windings, providing a secondary fluid channel enclosed by said helix;

whereby pressure in said tube, impelling said helix to unwind, tends to free said perforations from occluding organic deposits, and said secondary fluid channel, created upon restoration of the tightly wound helix, serves as a sump for spent fluid.

2. The catheter of claim 1 wherein the distal terminus of said tube is closed.

3. The catheter of claim 1 wherein said protrusions comprise a plurality of longitudinal ribs affixed to said wall.

4. The catheter of claim 1 wherein said tube is produced with a restoring set, providing said means for urging said tube into a helix configuration.

5. The catheter of claim 1 wherein a biocompatible spring with a helical restoring set is passed through a longitudinal passage in said tube, providing said means for urging said tube into a helix configuration.

6. The catheter of claim 1 wherein said tube is constructed from silicone or polyurethane thermoformable elastomer.

7. The catheter of claim 1 wherein said tube has an oval-shaped cross section with relatively flat surfaces.

8. The catheter of claim 1 wherein the distal portion of said tube is configured as a substantially straight tail.

9. The catheter of claim 1 further comprising means adjacent the proximal end of said tube for anchoring said catheter in the body.

10. The catheter of claim 9 wherein said anchoring means includes a cuff on said tube to encourage tissue ingrowth.

* * * * *